United States Patent
Tsukizawa et al.

(10) Patent No.: US 8,649,583 B2
(45) Date of Patent: Feb. 11, 2014

(54) PUPIL DETECTION DEVICE AND PUPIL DETECTION METHOD

(75) Inventors: Sotaro Tsukizawa, Kanagawa (JP); Kenji Oka, Kanagawa (JP)

(73) Assignee: Panasonic Corporation, Osaka (JP)

( * ) Notice: Subject to any disclaimer, the term of this patent is extended or adjusted under 35 U.S.C. 154(b) by 180 days.

(21) Appl. No.: 13/496,713

(22) PCT Filed: Jun. 15, 2011

(86) PCT No.: PCT/JP2011/003411
§ 371 (c)(1),
(2), (4) Date: Mar. 16, 2012

(87) PCT Pub. No.: WO2012/011221
PCT Pub. Date: Jan. 26, 2012

(65) Prior Publication Data
US 2012/0177266 A1   Jul. 12, 2012

(30) Foreign Application Priority Data
Jul. 20, 2010 (JP) ................................. 2010-162964

(51) Int. Cl.
*G06K 9/00* (2006.01)

(52) U.S. Cl.
USPC ........... 382/128; 382/117; 382/199; 382/162; 382/167; 348/241

(58) Field of Classification Search
None
See application file for complete search history.

(56) References Cited

U.S. PATENT DOCUMENTS 5,432,866 A *  7/1995 Sakamoto ...................... 382/128
5,561,289 A * 10/1996 Yamada et al. ................ 250/221
7,650,064 B2 *  1/2010 Isogai et al. .................... 396/18
8,041,118 B2 * 10/2011 Fowell ........................... 382/181
8,482,726 B2 *  7/2013 Mou ............................... 356/233
2012/0170027 A1 *  7/2012 Tsukizawa et al. ........... 356/124

FOREIGN PATENT DOCUMENTS

| JP | 02-213322 A | 8/1990 |
| JP | 07-248216 A | 9/1995 |
| JP | 2005-018405 A | 1/2005 |
| JP | 2008-246143 A | 10/2008 |
| JP | 2009-254525 A | 11/2009 |
| JP | 2010-220942 A | 10/2010 |
| WO | 2008/120635 A1 | 10/2008 |

OTHER PUBLICATIONS

Sakashita et al., Measurement of Cycloduction Movement Based on Fast Ellipse Detection, Jun. 2006, p. 558-565, Chubu University, DENSO Corporation.

* cited by examiner

*Primary Examiner* — Nancy Bitar
(74) *Attorney, Agent, or Firm* — Pearne & Gordon LLP

(57) ABSTRACT

A pupil detection device and a pupil detection method, which are capable of stably detecting the pupil by actively using information of cornea-reflected image even when most of the pupil is hidden by the cornea-reflected image. In pupil detection device (100), peripheral state evaluating section (105) sets a plurality of line segments having a reference point of a cornea-reflected image as one end and having a predetermined length, and calculates a luminance evaluation value based on luminance of each pixel in each line segment and reference luminance. Pupil center straight line calculation section (106) specifies a pupil center straight line passing through a center of a pupil image from among a plurality of line segments based on a luminance evaluation value. Pupil search section (107) detects a pupil image based on a luminance state around the pupil center straight line.

11 Claims, 17 Drawing Sheets

PUPIL DETECTION DEVICE AND PUPIL DETECTION METHOD

TECHNICAL FIELD

The present invention relates to a pupil detection device and a pupil detection method.

BACKGROUND ART

When line of sight detection or facial expression detection is performed from a face image under circumstances where it is difficult to secure sufficient illuminance like at night or in tunnels, a floodlight may be used to secure illuminance. In the case of using a floodlight, a cornea-reflected image generated as floodlight is projected on a cornea of an eyeball is observed on the eyeball. When an image of the cornea-reflected image (which may be hereinafter referred to as "cornea-reflected image") overlaps a pupil image, the pupil image may be hidden by the cornea-reflected image. Under this circumstance, it is difficult to detect the pupil image by a conventional pupil detecting technique, which is premised on the assumption that the pupil image is completely seen.

As a first method of coping with this problem, there is a method disclosed in Patent Literature 1. In the first method, a distribution of luminance in an eye area is calculated, and a negative edge and a positive edge corresponding thereto are searched based on a calculation result. In the above-described way, even though the cornea-reflected image appears in the pupil image, pupil detection can be performed.

Further, as a second method, there is a method disclosed in Patent Literature 2. In the second method, a super luminescent diode (SLD) is used as a floodlight. Thus, an area of a reflected image of a floodlight projected on glasses or the cornea can be reduced, and therefore pupil detection can be stably performed.

Furthermore, as a third method, there is a method disclosed in Non-Patent Literature 1. In the third method, a plurality of parallelograms are formed from edges of a pupil area, and voting is performed on the centers of the parallelograms. Then, the most voted coordinates are detected as the pupil center. Then, a pupil contour is detected from edges which are at equal distances from the detected pupil center.

CITATION LIST

Patent Literature

PTL 1
Japanese Patent Application Laid-Open No. 2-213322
PTL 2
Japanese Patent Application Laid-Open No. 7-248216

Non-Patent Literature

NPL 1
"Measurement of Cycloduction Movement Based on Fast Ellipse Detection", Yuusuke Sakashita, Hironobu Fujiyoshi, Yutaka Hirata, Hisanori Takamaru, Naoki Fukaya, SSII2006

SUMMARY OF INVENTION

Technical Problem

Meanwhile, in the first method described above, when the cornea-reflected image overlaps the pupil contour, an attempt to avoid a situation in which the cornea-reflected image overlaps the pupil contour has been made by changing the position of the floodlight. However, when a plurality of floodlights are used or when it is difficult to change the position of the floodlight, it is difficult to avoid a situation in which the cornea-reflected image overlaps the pupil contour, and thus it may be impossible to perform pupil detection.

Further, in the second method, an area where the pupil is hidden by the cornea-reflected image is reduced by reducing the physical size of the cornea-reflected image. However, when it is difficult to secure the sufficient resolution of an image, the size of the cornea-reflected image is substantially the same as the size of the pupil image, regardless of the physical size of the cornea-reflected image. For example, in the principle of a digital image, the diameter of the cornea-reflected image on the image is one pixel or more. However, when the resolution is low, the pupil diameter may be reduced up to about one pixel at a minimum. For this reason, when the cornea-reflected image overlaps the pupil, a "hidden area" where the pupil image is hidden by the cornea-reflected image increases on the image, and thus it is difficult to perform pupil detection.

Furthermore, in the third method, four points are extracted from each of edge pixels which are pupil contour candidates to generate a plurality of parallelograms, and a pixel having the most points which become the center of the parallelogram is set as the pupil center. However, when an edge at the position symmetric to the pupil center is not observed, it is rare for the center of the parallelogram to be positioned at the pupil center portion. For this reason, when a half or more of the pupil is hidden by the cornea-reflected image, it is difficult to perform pupil detection.

The present invention is made in light of the foregoing, and it is an object of the present invention to provide a pupil detection device and a pupil detection method, which are capable of stably detecting the pupil even when most of the pupil is hidden by the cornea-reflected image.

Solution to Problem

A pupil detection device of the present invention is a pupil detection device that detects a pupil image in an eye area image and includes: a first detection section that detects a cornea-reflected image that is a high-luminance image area of the eye area image; an evaluation value calculation section that sets a plurality of line segments having a reference point of the cornea-reflected image as one end and having a predetermined length, and calculates a luminance evaluation value based on luminance of each pixel in each line segment and reference luminance; a specifying section that specifies a pupil center straight line passing through a center of the pupil image from among the plurality of line segments based on the luminance evaluation value; and a second detection section that detects the pupil image based on a luminance state around the pupil center straight line or a luminance state of the pupil center straight line.

A pupil detection method of the present invention is a pupil detection method of detecting a pupil image in an eye area image and includes detecting a cornea-reflected image that is a high-luminance image area of the eye area image, setting a plurality of line segments having a reference point of the cornea-reflected image as one end and having a predetermined length, calculating a luminance evaluation value based on luminance of each pixel in each line segment and reference luminance, specifying a pupil center straight line passing through a center of the pupil image from among the plurality of line segments based on the luminance evaluation value, and detecting the pupil image based on a luminance state around the pupil center straight line or a luminance state on the pupil center straight line.

Advantageous Effects of Invention

According to the present invention, it is possible to provide a pupil detection device and a pupil detection method, which are capable of stably detecting the pupil by actively using information of a cornea-reflected image, even when the most of the pupil is hidden by the cornea-reflected image.

DESCRIPTION OF EMBODIMENTS

Figure 1:
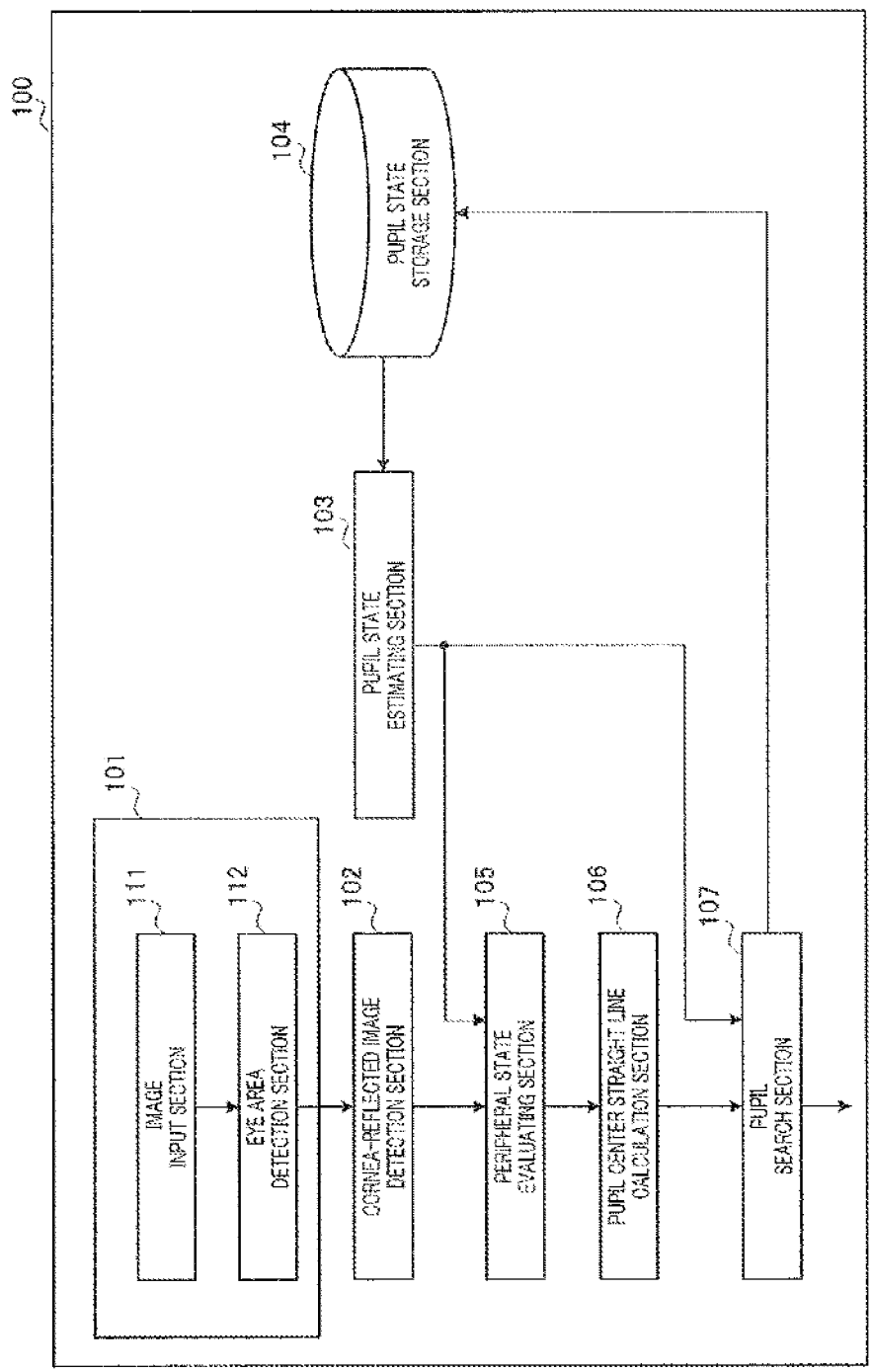
FIG. 1 is a block diagram illustrating a configuration of a pupil detection device according to Embodiment 1 of the present invention.

Hereinafter, embodiments of the invention will be described in detail with reference to the drawings. In the following embodiments, like reference numerals denote like components, and thus the redundant description will not be repeated.

Embodiment 1

Configuration of Pupil Detection Device 100

FIG. 1 is a block diagram illustrating a configuration of pupil detection device 100 according to Embodiment 1 of the present invention. For example, pupil detection device 100 is installed in a cabin of a vehicle, and is connected to a line-of-sight detection device and then used. The line-of-sight detection device determines a pupil position based on a detection result of pupil detection device 100, and detects a line-of-sight direction of a driver. In the following, a description will be made in connection with, particularly, an example in which pupil detection device 100 is applied to the line-of-sight detection device.

Referring to FIG. 1, pupil detection device 100 includes eye area image acquisition section 101, cornea-reflected image detection section 102, pupil state estimating section 103, pupil state storage section 104, peripheral state evaluating section 105, pupil center straight line calculation section 106, and pupil search section 107.

Eye area image acquisition section 101 acquires an eye area image, and outputs the eye area image to cornea-reflected image detection section 102.

Specifically, eye area image acquisition section 101 includes image input section 111 and eye area detection section 112.

Image input section 111 photographs a photographing target (i.e., a person herein). This target image data is output to eye area detection section 112.

Image input section 111 is installed at the front of a driver's seat such as on a steering wheel of the automobile or on a dashboard. By doing so, the face of the driver while driving is photographed by image input section 111.

Eye area detection section 112 detects the eye area image from the target image received from image input section 111.

Figure 2:
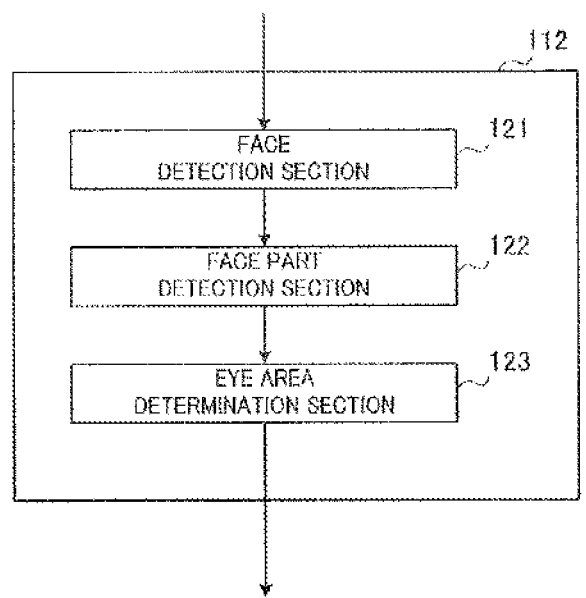
FIG. 2 is a block diagram showing a configuration of an eye area detection section.

Specifically, eye area detection section 112 includes face detection section 121, face part detection section 122, and eye area determination section 123, as shown in FIG. 2.

Face detection section 121 detects a face image from the target image received from image input section 11, and outputs the face image data to face part detection section 122.

Face part detection section 122 detects a group of face parts (i.e., a tail of the eye, an inner corner of the eye, etc.) from the face image received from face detection section 121, and outputs positional coordinates of each face part to eye area determination section 123.

Eye area determination section 123 determines the position and size of the eye area image, based on the positional coordinates of each face part received from face part detection section 122. The position and the size of the eye area image are output to cornea-reflected image detection section 102 as an eye area image detection result, together with the target image output from image input section 111. It is to be noted that the position and size of the eye area image are calculated for each of the right and left eyes.

Returning to FIG. 1; cornea-reflected image detection section 102 detects a cornea-reflected image from the target image data received from eye area image acquisition section 101, and outputs information related to the detected cornea-reflected image to peripheral state evaluating section 105. The information related to the cornea-reflected image includes coordinates of the center of the cornea-reflected image area.

Peripheral state evaluating section 105 calculates a "luminance evaluation value" in a radiation direction, when viewed on the basis of the cornea-reflected image. In other words, peripheral state evaluating section 105 calculates a correspondence relation between the luminance evaluation value, and an angle between the calculated radiation direction of the luminance evaluation value and a reference direction.

Specifically, peripheral state evaluating section 105 sets a reference point in the cornea-reflected image detected by cornea-reflected image detection section 102, and sets a plurality of line segments having the reference point as one end and a predetermined length. The plurality of line segments are sequentially set by way of rotating by a predetermined angle each time from the reference direction. The predetermined length of the line segment is identical to the estimated diameter of the pupil image (which may be hereinafter referred to as "estimated pupil diameter"), since it is herein assumed that the cornea-reflected image overlaps the pupil image. The estimated pupil diameter is estimated by pupil state estimating section 103. Further, when processing is performed considering that the cornea-reflected image does not overlap the pupil image, the length of the line segment is preferably set to be larger than the estimated pupil diameter.

Then, peripheral state evaluating section 105 calculates the luminance evaluation value, based on luminance of pixels in the line segments and reference luminance. In detail, peripheral state evaluating section 105 compares luminance of each pixel in each line segment with the reference luminance, extracts pixels having luminance lower than the reference luminance, and calculates a total sum of differences between luminance of all extracted pixels and the reference luminance as the luminance evaluation value. That is, the luminance evaluation value may be calculated using the following equation (1).

(Equation 1)

$$V = \sum_{L} (B < S ? S - B : 0) \quad [1]$$

where V represents the luminance evaluation value, S represents sclera average luminance used as the reference luminance, B represents luminance of each pixel on the line segment, and L represents the line segment.

Pupil center straight line calculation section 106 specifies a line segment (which may be hereinafter referred to as "pupil center straight line") passing through the center of the pupil image, based on the luminance evaluation value calculated by peripheral state evaluating section 105. Specifically, pupil center straight line calculation section 106 specifies the line segment, which is the largest in the luminance evaluation value calculated by peripheral state evaluating section 105, as the pupil center straight line.

Pupil search section 107 searches for a pupil image, based on a luminance state around the pupil center straight line. Specifically, pupil search section 107 searches for the pupil image area by sequentially setting pupil image area candidates, based on the pupil center straight line specified by pupil center straight line calculation section 106 and a diameter candidate group including the estimated pupil diameter described above, and then detecting the pupil image area (that is, an area that appears most similar to the pupil image area) from the pupil image area candidate group based on the luminance states of the pupil image area candidates.

Specifically, pupil search section 107 sets a circle, whose center is present on the pupil center straight line and whose diameter is one diameter candidate within the diameter candidate group, as the pupil image area candidate. Pupil search section 107 then calculates a luminance state index of the corresponding pupil image area candidate. In this case, average luminance of a pixel group having luminance lower than the reference luminance, among pixel groups of the set pupil image area candidate is used as the luminance state index. That is, the luminance state index may be calculated using the following equation 2.

(Equation 2)

$$X = \frac{\sum_{P}(B < S ? B : 0)}{\sum_{P}(B < S ? 1 : 0)} \quad [2]$$

where, X represents the luminance state index of the pupil image area candidate, and P represents the pupil image area candidate. That is, P represents a circle whose center is present on the pupil center straight line and whose diameter is one diameter candidate within the diameter candidate group. In other words, in the denominator of equation 2, the number of pixels having luminance lower than the reference luminance in the pupil image area candidate is counted, whereas in the numerator, a total sum of luminance of pixels having luminance lower than the reference luminance in the pupil image area candidate is obtained.

The luminance state index is obtained on each pupil image area candidate (that is, each of pupil image area candidates which has different combinations of a central position and a diameter candidate), and the pupil image area candidate having the smallest luminance state index among the pupil image area candidate group is specified as the pupil image area.

Information related to the specified pupil image area (that is, information related to the central position and the diameter) is stored in pupil state storage section 104, and is used for a line-of-sight detecting process in a line-of-sight detection section (not illustrated), which is a functional section of a subsequent stage. Here, a plurality of diameter candidates are prepared, however, only the estimated pupil diameter may be used. In this case, under photographing circumstances where a change in the pupil diameter is small, the pupil detection accuracy can be also maintained, and a processing amount can be reduced.

Pupil state storage section 104 stores the information related to the pupil image area detected by pupil search section 107 (that is, information related to the central position and the diameter) in association with an imaging time of a target image used for detection of the pupil image area.

Pupil state estimating section 103 estimates the current diameter of the pupil from a previously detected pupil diameter (that is, the diameter of the pupil image area) stored in pupil state storage section 104. The estimated pupil diameter is output to peripheral state evaluating section 105 and pupil search section 107.

[Operation of Pupil Detection Device 100]

Figure 3:
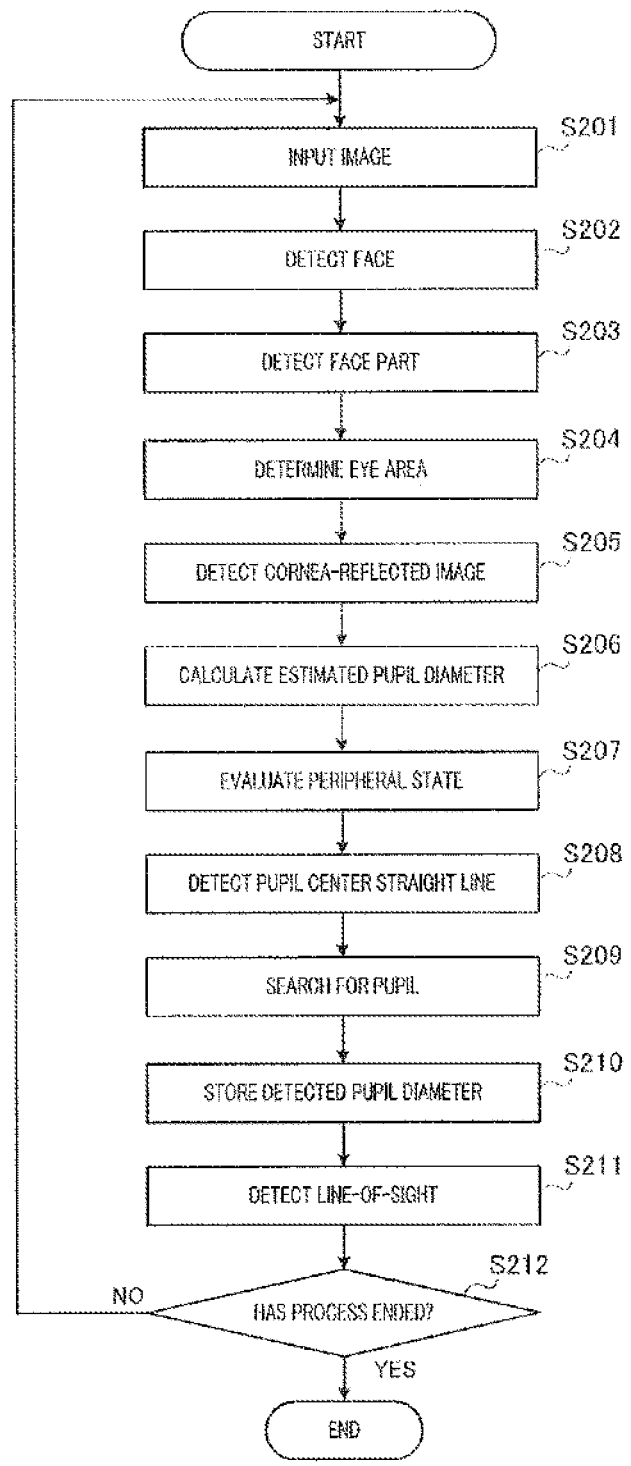
FIG. 3 is a flowchart for describing an operation of the pupil detection device.

A description will be made in connection with an operation of pupil detection device 100 having the above configuration. FIG. 3 is a flowchart for describing an operation of pupil detection device 100. The flowchart in FIG. 3 contains a processing flow in the aforementioned line-of-sight detection apparatus.

The processing flow shown in FIG. 3 starts at the same time as a start of a photographing operation. The photographing operation may be started by an operation of a user or by a certain external signal as a trigger.

<Image Acquisition Process>

At step S201, image input section 111 photographs a photographing target (i.e., a person herein). By doing so, a target image is acquired.

As image input section 111, a digital camera having a CMOS image sensor and a lens is assumed, for example. Thus, an image or the like in PPM (Portable Pix Map) file formal photographed at image input section 111 is temporarily stored in a image storage section (not illustrated) (e.g., a memory space of a PC) contained in image input section 111, and is thereafter output to eye area detection section 112 as it is in PPM file format.

<Face image Detection Process>

Figure 4:
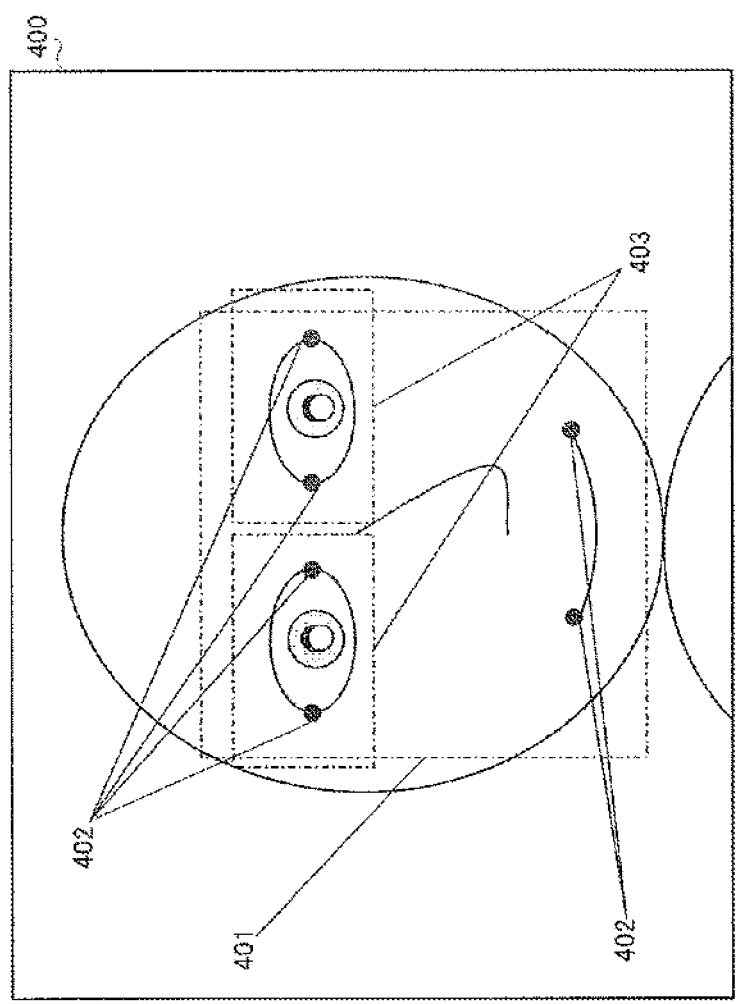
FIG. 4 shows a face image as a target image.

At step S202, face detection section 121 detects a face image from the target image received from image input section 111. FIG. 4 shows the face image as the target image. It is to be noted that, in the photographed face image, the horizontal direction of the image is an X axis, the vertical direction of the image is a Y axis, and one pixel is one coordinate point, for example.

In the face area detection processing, a candidate of a feature image (that is, a feature image candidate) is extracted from the input image, and the extracted feature image candidate is compared with a feature image representing a face area prepared in advance, to detect a feature image candidate having a high degree of similarity. Referring to the amount of Gabor features of an average face obtained in advance and the amount of Gabor features extracted by scanning of the input image, the degree of similarity is derived as a reciprocal of the absolute value of the difference between such amounts.

In this case, face detection section 121 identifies as face image 401, an area having the highest correlation in image 400 of FIG. 4, in comparison with a template prepared in advance. It is noted that the face area detection processing may be performed by detecting a flesh color area from the image (that is, flesh color area detection), detecting an elliptic part (that is, ellipse detection), or using a statistical pattern identification method. Any method may be adopted as long as it is a technique enabling the above face detection.

<Face Part Detection Process>

At step S203, face part detection section 122 detects a group of face parts (i.e., a corner of the mouth, a tail of the eye, an inner corner of the eye, etc.) from the face image received from face detection section 121, and outputs positional coordinates of each face part to eye area determination section 123. A search area for the group of face parts is face area 401 identified at step S202. FIG. 4 shows face parts group 402.

In the face parts group detection processing, two-dimensional coordinates of end points of the face parts such as the corner of the mouth, the outer corner of the eye, and the inner corner of the eye and nasal cavities are detected, e.g., with use of a separability filter. Also, by making a learning section learn positional correspondence relations between plural face images and face parts corresponding to the face images in advance, face part detection section 122 may detect a position with the highest likelihood in relation to each of the correspondence relations, when a face part when face image 401 is input. Alternatively, face part detection section 122 may search a face part from face image 401 with use of a standard face part template.

<Eye Area Determination Process>

In step S204, eye area determination section 123 determines an eye area, based on the face image received from face detection section 121 and a group of face parts received from face part detection section 122.

In the eye area determining processing, for each of the right and left eyes, rectangular area 403 containing the tail of the eye and the inner corner of the eye is determined as an eye area, and coordinates of an upper left end point and a lower right end point both, both of which have a rectangular form, are obtained as eye area information, for example.

<Cornea-Reflected Image Detecting Process>

Figure 5:
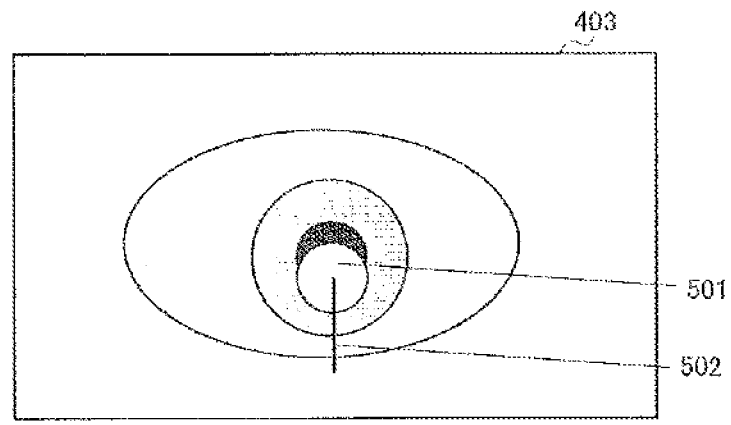
FIG. 5 is a diagram for describing a cornea-reflected image detecting process and a luminance evaluation value calculating process.

In step S205, cornea-reflected image detection section 102 detects a cornea-reflected image, based on a face image received from face detection section 121 and eye area information received from eye area determination section 123. Specifically, cornea-reflected image detection section 102 detects center coordinates of cornea-reflected image 501 in eye area 403 as illustrated in FIG. 5. For example, cornea-reflected image detection section 102 creates a luminance distribution of eye area 403, detects, using the created luminance distribution, an area that has a predetermined luminance or more and has the size within a range of a predetermined size as a cornea-reflected image, and sets the centroid of the detected area as the center of the cornea-reflected image.

<Estimated Pupil Diameter Calculating Process>

In step S206, pupil state estimating section 103 calculates the estimated pupil diameter, based on the previously detected pupil diameter stored in pupil state storage section 104 as the current pupil diameter. the estimated pupil diameter is such that when the speed at which the pupil diameter changes is calculated based on a history of the previously detected pupil diameters, and the pupil diameter change speed is maintained. However, a calculation of the estimated pupil diameter is not limited to the above described method. For example, human's average maximum miosis speed may be used when the change in the pupil diameter is expected to be reduced, whereas a maximum mydriasis speed may be used when the change in the pupil diameter is expected to be increased. Alternatively, the estimated pupil diameter may be calculated by state estimation using the Kalman filter and the like.

<Luminance Evaluation Value Calculating Process>

Figure 6:
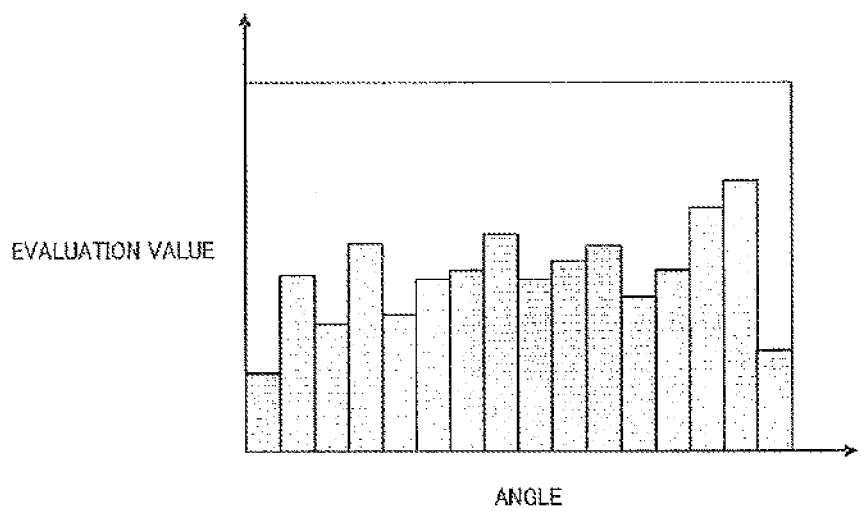
FIG. 6 is a diagram illustrating an example of a correspondence relation between a luminance evaluation value and an angle between a calculated radiation direction of the luminance evaluation value and a reference direction.

In step S207, peripheral state evaluating section 105 calculates a correspondence relation between the luminance evaluation value and an angle between the calculated radiation direction of the luminance evaluation value and the reference direction, based on the luminance distribution of the image area including the cornea-reflected image created by cornea-reflected image detection section 102. FIG. 6 illustrates an example of the correspondence relation between the luminance evaluation value and the angle between the calculated radiation direction of the luminance evaluation value and the reference direction.

Specifically, peripheral state evaluating section 105 first calculates an average luminance of an area which is distant from the center of the cornea-reflected image by an average cornea radius (for example, 5 mm) or more, in the eye area, as sclera average luminance. The sclera average luminance is used as the reference luminance.

Next, as illustrated in FIG. 5, peripheral state evaluating section 105 sets a reference point (here, the center of the cornea-reflected image area) of the cornea-reflected image detected by cornea-reflected image detection section 102, and sets line segment 502 that has the reference point as its one end and has the length of the estimated pupil diameter.

Then, peripheral state evaluating section 105 calculates the luminance evaluation value based on luminance of the pixels in line segments 502 and the reference luminance. The luminance evaluation value is calculated such that pixels having luminance lower than the reference luminance are extracted, and a total sum of differences between the luminance of all extracted pixels and the reference luminance is calculated.

Figure 7:
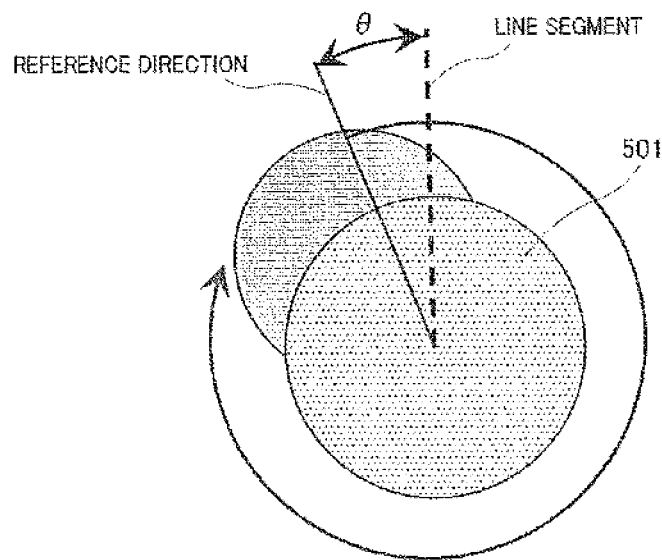
FIG. 7 is a diagram for describing the luminance evaluation value calculating process.

This calculation process is performed on each of a plurality of line segments 502 which are sequentially set by way of rotating by a predetermined angle each time from the reference direction as illustrated in FIG. 7.

Here, an image corresponding to the cornea or an image area where ambient light is projected on glasses or the cornea is higher in luminance than an image corresponding to the pupil. Thus, by extracting only pixels having luminance lower than the reference luminance, using luminance of an image area corresponding to the sclera as a reference, influence of pixels which are least likely to be an image area corresponding to the pupil can be excluded. Further, by calculating the luminance evaluation value only for pixels of low luminance which are likely to be an image area corresponding to the pupil, an evaluation value which enhances the detection accuracy of the pupil center straight line can be obtained.

<Pupil Center Straight Line Detecting Process>

In step S208, pupil center straight line calculation section 106 specifies a pupil center straight line, based on the luminance evaluation value calculated by peripheral state evaluating section 105. Specifically, pupil center straight line calculation section 106 specifies a line segment having the highest luminance evaluation value calculated by peripheral state evaluating section 105, as the pupil center straight line. Further, an angle of the pupil center straight line with respect to the reference direction may be detected by weight-averaging a range having the highest sum of luminance evaluation values in a predetermined angle range. In this case, a straight line that passes through the center of the cornea-reflected image area and extends in a detection angle direction is set as the pupil center straight line.

<Pupil Search Process>

Figure 8:
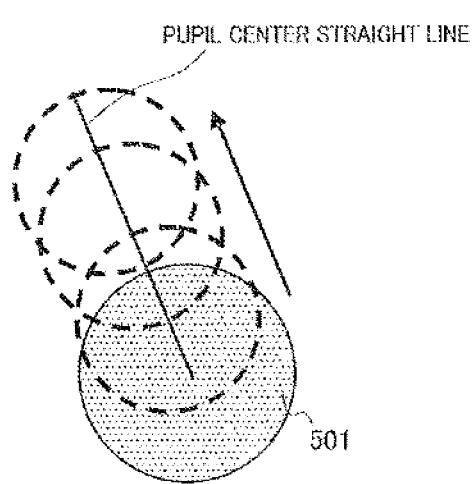
FIG. 8 is a diagram for describing a pupil search process.

In step S209, pupil search section 107 searches for the pupil image area by sequentially setting pupil image area candidates based on the pupil center straight line specified by pupil center straight line calculation section 106 and the diameter candidate group including the estimated pupil diameter, and then detecting the pupil image area (that is, an area that appears most similar to the pupil image area) from the pupil image area candidate group based on the luminance states of the pupil image area candidates as illustrated in FIG. 8. FIG. 8 illustrates only the pupil image area candidate group of the estimated pupil diameter.

Specifically, pupil search section 107 sets a circle whose center is present on the pupil center straight line and whose diameter is one diameter candidate within the diameter candidate group as the pupil image area candidate, and calculates the luminance state index of the pupil image area candidate. In this case, among pixel groups of the set pupil image area candidate, average luminance of a pixel group having luminance lower than the reference luminance is used as the luminance state index.

<Pupil Image Area Information Storing Process>

In step S210, pupil state storage section 104 stores information related to the pupil image area detected by pupil search section 107 (that is, information related to the central position and the diameter) in association with the imaging time of the target image used for detection of the pupil image area.

<Line-of-Sight Detecting Process>

In step S211, the line-of-sight detection section (not illustrated) detects a line of sight.

The line-of-sight detection is calculated from a face direction vector representing a direction of the face in the front direction calculated from the coordinates of face parts group 402 and a line-of-sight direction vector with respect to the front direction of the face calculated from the coordinates of the tail of the eye, the inner corner of the eye, and a pupil center.

The face direction vector is calculated, e.g., in the following procedures. First, three-dimensional coordinates of the group of face parts of the driver obtained in advance are converted by rotation and translation. Subsequently, the converted three-dimensional coordinates are projected on the target image used for pupil detection. Subsequently, rotation and translation parameters that best correspond to the group of face parts detected at step S203 are calculated. A set consisting of a vector representing a direction to which the driver's face is directed when the three-dimensional coordinates of the group of face parts of the driver are obtained in advance, and a vector rotated by the determined rotation parameter is the face direction vector.

Also, the line-of-sight direction vector is calculated, e.g., in the following procedures. First, in a case where his/her face is directed in a predetermined direction, three-dimensional coordinates of the group of face parts and the pupil center of the driver, when the driver looks in the same direction as the face direction, are stored. The pupil center is detected, e.g., by deriving a centroid of pixels having predetermined luminance or lower in the eye area. Subsequently, a position distanced by a predetermined distance in a direction opposite to the line-of-sight direction from the detected three-dimensional coordinates of the pupil is calculated as an eyeball center position. At this time, although it is appropriate that the aforementioned predetermined distance should be 12 mm or so, which is a radius of an eyeball of a general adult, any value other than the above value may be used. Subsequently, three-dimensional coordinates of the eyeball center at the time of detection are derived with use of the rotation and translation parameters of the face obtained at the time of calculation of the face direction vector. Subsequently, under the assumption that the pupil exists on a sphere centering on the eyeball center and having a radius that has the aforementioned predetermined distance, a position of the detected pupil center on the above sphere is searched. Finally, a vector connecting the eyeball center to the searched point on the sphere is calculated as the line-of-sight direction vector.

<Termination Determining Process>

At step S212, an end determination is performed. Termination determination may be performed when a termination instruction is manually input or may be performed by pupil detection device 100 using any external signal as a trigger.

In a case where it is determined at step S212 that processing is ended, processing in FIG. 3 is ended.

As described above, according to the present embodiment, in pupil detection device 100, peripheral state evaluating section 105 sets a plurality of line segments that have the reference point of the cornea-reflected image as one end and have a predetermined length, and calculates the luminance evaluation value based on luminance of pixels in the line segments and the reference luminance. Pupil center straight line calculation section 106 specifies a pupil center straight line passing through the center of the pupil image from among a plurality of line segments based on the luminance evaluation value. Pupil search section 107 detects a pupil image based on a luminance state around the pupil center straight line.

As described above, after the pupil center straight line is specified based on the luminance evaluation value in the line segment set using the cornea-reflected image as a reference, the pupil image is detected based on the luminance state around the pupil center straight line. Thus, stable pupil detection can be realized using information of the cornea-reflected image actively.

Further, peripheral state evaluating section 105 compares luminance of each pixel in each line segment with the reference luminance, extracts pixels having luminance lower than the reference luminance, and calculates a total sum of differences between luminance of all extracted pixels and the reference luminance as the luminance evaluation value.

Further, pupil center straight line calculation section 106 specifies the line segment having the highest luminance evaluation value as the pupil center straight line.

Furthermore, the estimated pupil diameter estimated from the pupil diameters previously detected by pupil state estimating section 103 is used as the predetermined length of the set line segment. Here, a specified value which is previously determined may be used as the predetermined length.

In addition, sclera average luminance may be used as the reference luminance.

Embodiment 2

In Embodiment 2, sclera average luminance most recently calculated based on the detected pupil image is used as the reference luminance.

Figure 9:
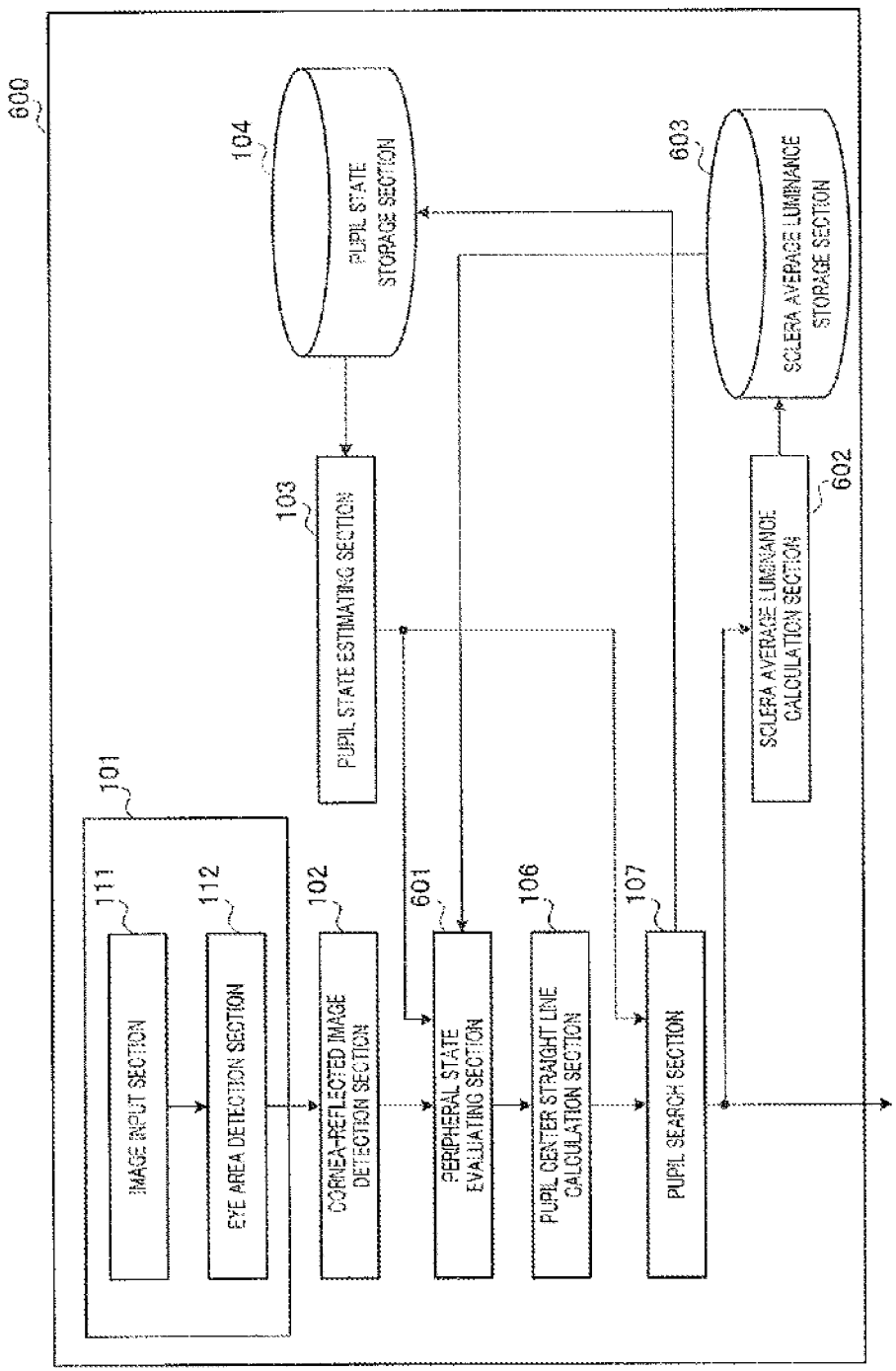
FIG. 9 is a block diagram illustrating a configuration of a pupil detection device according to Embodiment 2 of the present invention.

FIG. 9 is a block diagram illustrating a configuration of pupil detection device 600 according to Embodiment 2 of the present invention. Referring to FIG. 9, pupil detection device 600 includes peripheral state evaluating section 601, sclera average luminance calculation section 602, and sclera average luminance storage section 603.

Peripheral state evaluating section 601 calculates the correspondence relation between the luminance evaluation value and an angle between the calculated radiation direction of the luminance evaluation value and the reference direction, similarly to peripheral state evaluating section 105. Here, peripheral state evaluating section 601 uses sclera average luminance, which has been most recently calculated based on the detected pupil image, received from sclera average luminance storage section 603, as the reference luminance.

Sclera average luminance calculation section 602 calculates the sclera average luminance using coordinates of the pupil center detected by pupil search section 107, and outputs the calculated sclera average luminance to sclera average luminance storage section 603.

Sclera average luminance storage section 603 stores the sclera average luminance calculated by sclera average luminance calculation section 602 in association with the imaging time of the target image used for a calculation of the sclera average luminance.

Figure 10:
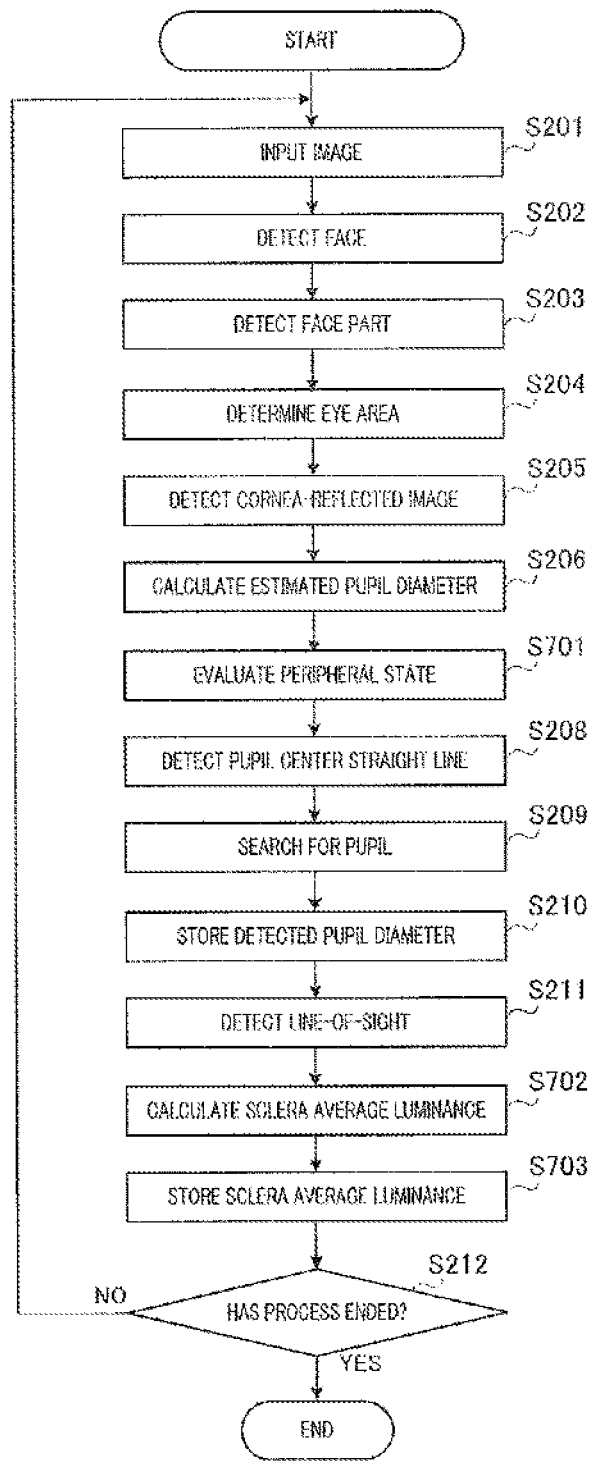
FIG. 10 is a flowchart for describing an operation of the pupil detection device.

Next, a description will be made in connection with an operation of pupil detection device 600 having the above configuration. FIG. 10 is a flowchart for describing an operation of pupil detection device 600.

In step S701, peripheral state evaluating section 601 calculates the correspondence relation between the luminance evaluation value and an angle between the calculated radiation direction of the luminance evaluation value and the reference direction, using the sclera average luminance most recently calculated based on the detected pupil image, as the reference luminance.

In step S702, sclera average luminance calculation section 602 calculates the sclera average luminance of the target image based on the target image, the cornea-reflected image calculated in step S205, and the pupil center and the detected pupil diameter calculated in step S209.

Specifically, average luminance of pixels, excluding pixels having luminance equal to or higher than that of the cornea-reflected image in the eye area and pixels included in a circle that has the pupil center as its center and the detected pupil diameter as its diameter, is set as the sclera average luminance.

In step S703, sclera average luminance storage section 603 stores the sclera average luminance calculated in step S702 in association with the imaging time of target image used for a calculation of the sclera average luminance.

As described above, according to Embodiment 2, in pupil detection device 600, peripheral state evaluating section 601 calculates the luminance evaluation value using the sclera average luminance most recently calculated based on the detected pupil image as the reference luminance.

Accordingly, the pupil detection accuracy can be improved.

Embodiment 3

In Embodiment 3, the diameter candidate set in the pupil search process is adjusted according to the illuminance.

Figure 11:
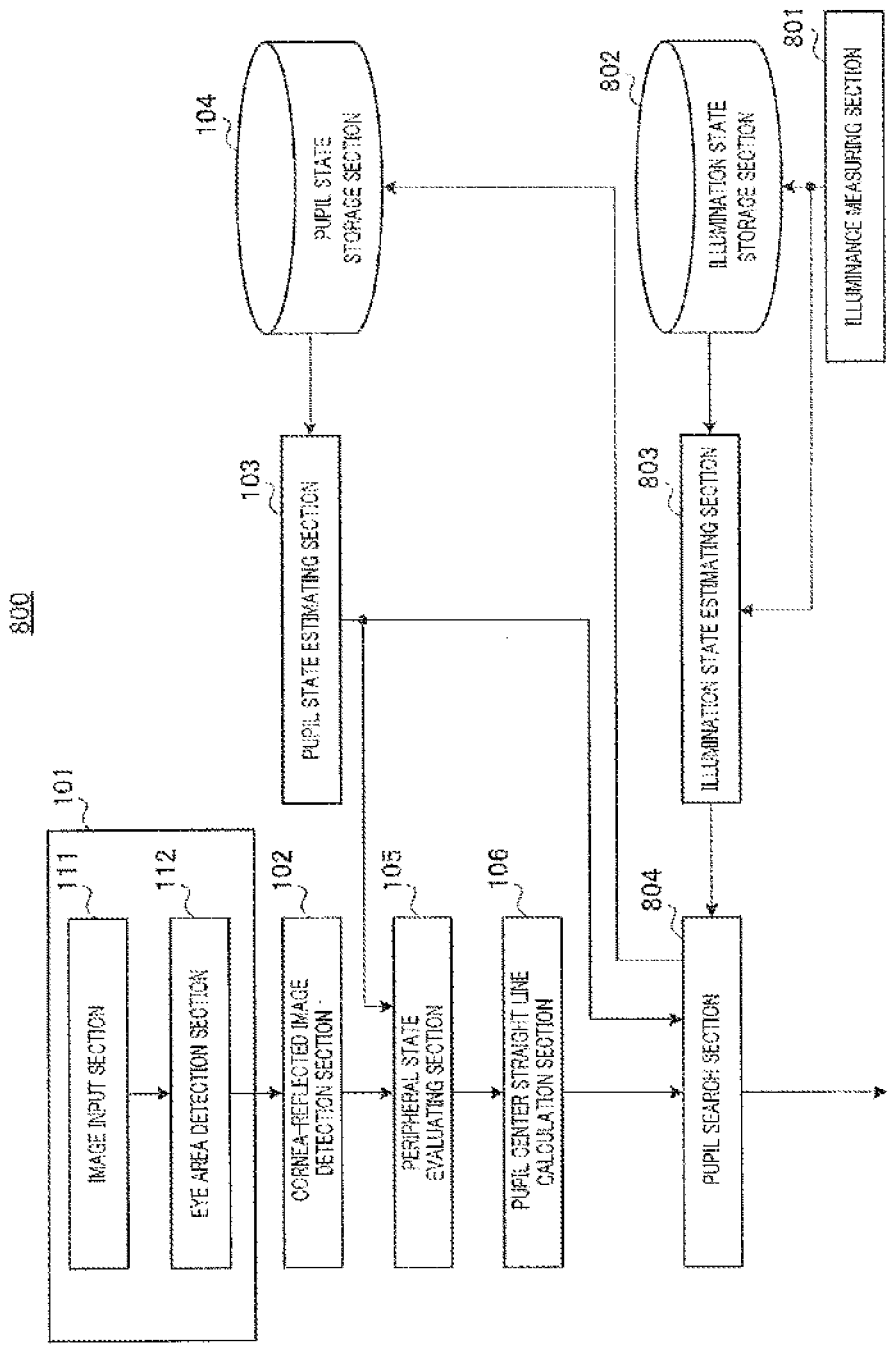
FIG. 11 is a block diagram illustrating a configuration of a pupil detection device according to Embodiment 3 of the present invention.

FIG. 11 is a block diagram illustrating a configuration of pupil detection device 800 according to Embodiment 3 of the present invention. Referring to FIG. 11, pupil detection device 800 includes illuminance measuring section 801, illumination state storage section 802, illumination state estimating section 803, and pupil search section 804.

Illuminance measuring section 801 measures illuminance at the time of photographing of the target image, and outputs the measured illuminance to illumination state storage section 802 and illumination state estimating section 803.

Illumination state storage section 802 stores the illuminance received from illuminance measuring section 801 in association with a photographing time.

Illumination state estimating section 803 compares first illuminance received from illuminance measuring section 801 with second illuminance, which has been measured directly before the first illuminance, stored in illumination state storage section 802, and outputs a comparison result to pupil search section 804.

Similarly to pupil search section 107 of Embodiment 1, pupil search section 804 searches for the pupil image area by sequentially setting pupil image area candidates based on the pupil center straight line specified by pupil center straight line calculation section 106 and the diameter candidate group including the estimated pupil diameter, and then detecting the pupil image area (that is, an area that appears most similar to the pupil image area) from the pupil image area candidate group based on the luminance states of the pupil image area candidates.

Here, pupil search section 804 adjusts the diameter candidate based on information related to the comparison result received from illumination state estimating section 803.

Specifically, when the first illuminance is lower than the second illuminance (that is, when the current illuminance is lower than the immediately previous illuminance), pupil search section 804 increases the diameter candidate. However, when the first illuminance is higher than the second illuminance, pupil search section 804 decreases the diameter candidate.

Figure 12:
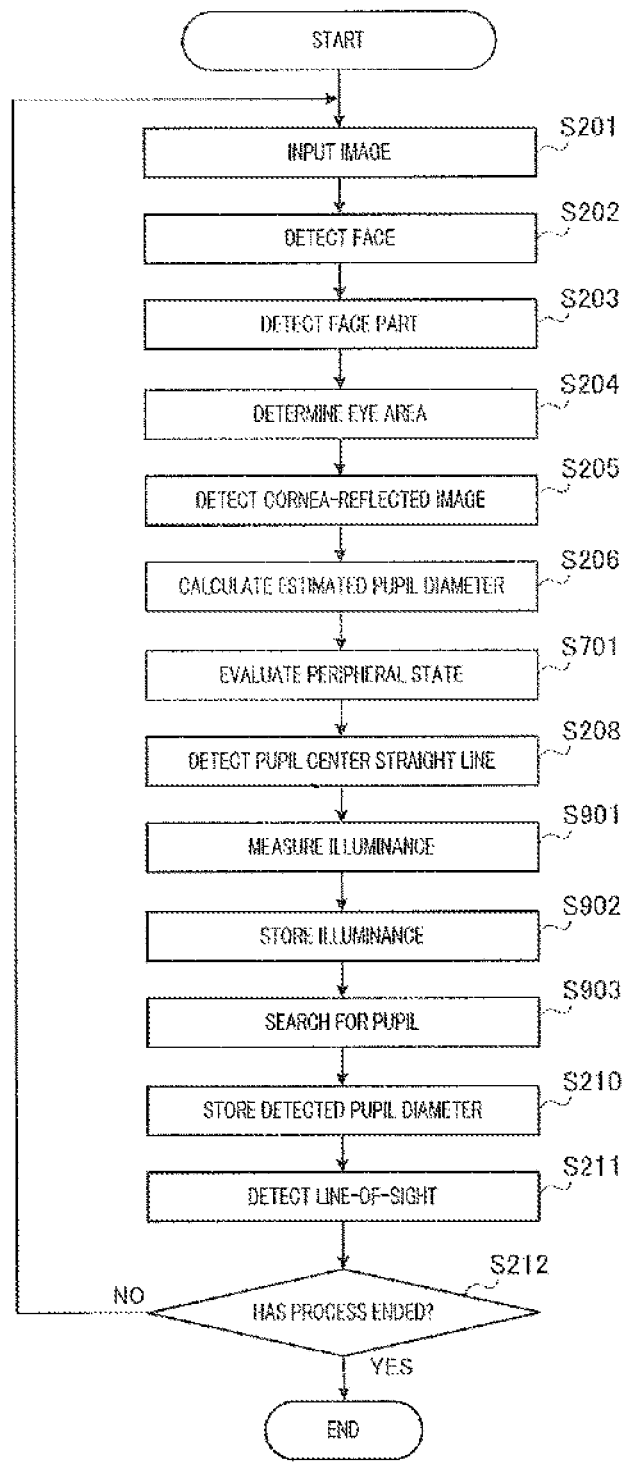
FIG. 12 is a flowchart for describing an operation of pupil detection device.

Next, a description will be made in connection with an operation of pupil detection device 800 having the above configuration. FIG. 12 is a flowchart for describing an operation of pupil detection device 800.

In step S901, illuminance measuring section 801 measures illuminance of photographing circumstances.

In step S902, illumination state storage section 802 stores the illuminance measured in step S901 in association with the imaging time of the target image.

In step S903, pupil search section 804 searches for the pupil image area by adjusting the diameter candidate based on information related to the comparison result received from illumination state estimating section 803, sequentially setting pupil image area candidates based on the pupil center straight line specified by pupil center straight line calculation section 106 and the adjusted diameter candidate, and then detecting the pupil image area from the pupil image area candidate group based on the luminance states of the pupil image area candidates.

As described above, according to the present embodiment, in pupil detection device 800, pupil search section 804 adjusts the diameter candidate based on the illuminance at the time of photographing of the target image.

Since the diameter candidate in which the pupil state at the time of photographing of the target image is reflected can be set, therefore, a time taken for pupil detection can be reduced.

Embodiment 4

Embodiment 4 relates to a modification of a method of specifying the pupil center straight line, based on the correspondence relation between the luminance evaluation value and the angle between the calculated radiation direction of the luminance evaluation value and the reference direction.

Figure 13:
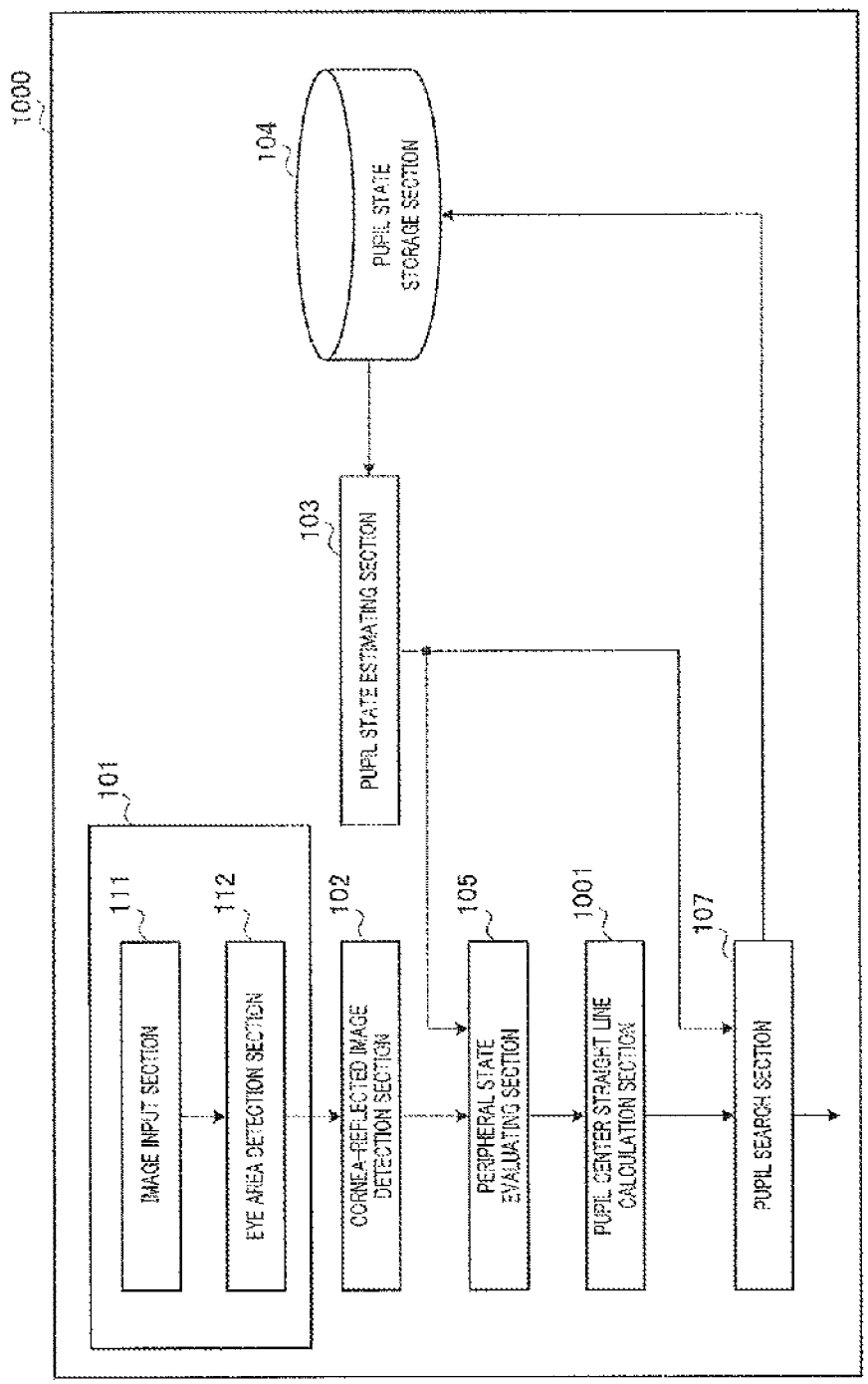
FIG. 13 is a block diagram illustrating a configuration of a pupil detection device according to Embodiment 4 of the present invention.

FIG. 13 is a block diagram illustrating a configuration of pupil detection device 1000 according to Embodiment 4 of the present invention. Referring to FIG. 13, pupil detection device 1000 includes pupil center straight line calculation section 1001.

Pupil center straight line calculation section 1001 specifies the pupil center straight line based on the luminance evaluation value calculated by peripheral state evaluating section 105. Specifically, pupil center straight line calculation section 1001 sequentially sets an average calculation range having a predetermined angle range while shifting the reference angle, and calculates an average value of the luminance evaluation values associated by the above described correspondence relation with respect to an angle belonging to each average calculation range. For example, the average calculation range is ±3 centering on the reference angle. Then, pupil center straight line calculation section 1001 specifies the line segment corresponding to the reference angle of the average calculation range having the highest average value, as the pupil center straight line.

As described above, by calculating the average value of the luminance evaluation values in the average calculation range having a predetermined angle range, the evaluation value in which not only the reference angle but also a state of a peripheral range thereof are considered can be obtained.

Embodiment 5

Similarly to Embodiment 4, Embodiment 5 relates to a modification of a method of specifying the pupil center straight line, based on the correspondence relation between the luminance evaluation value and the angle between the calculated radiation direction of the luminance evaluation value and the reference direction.

Figure 14:
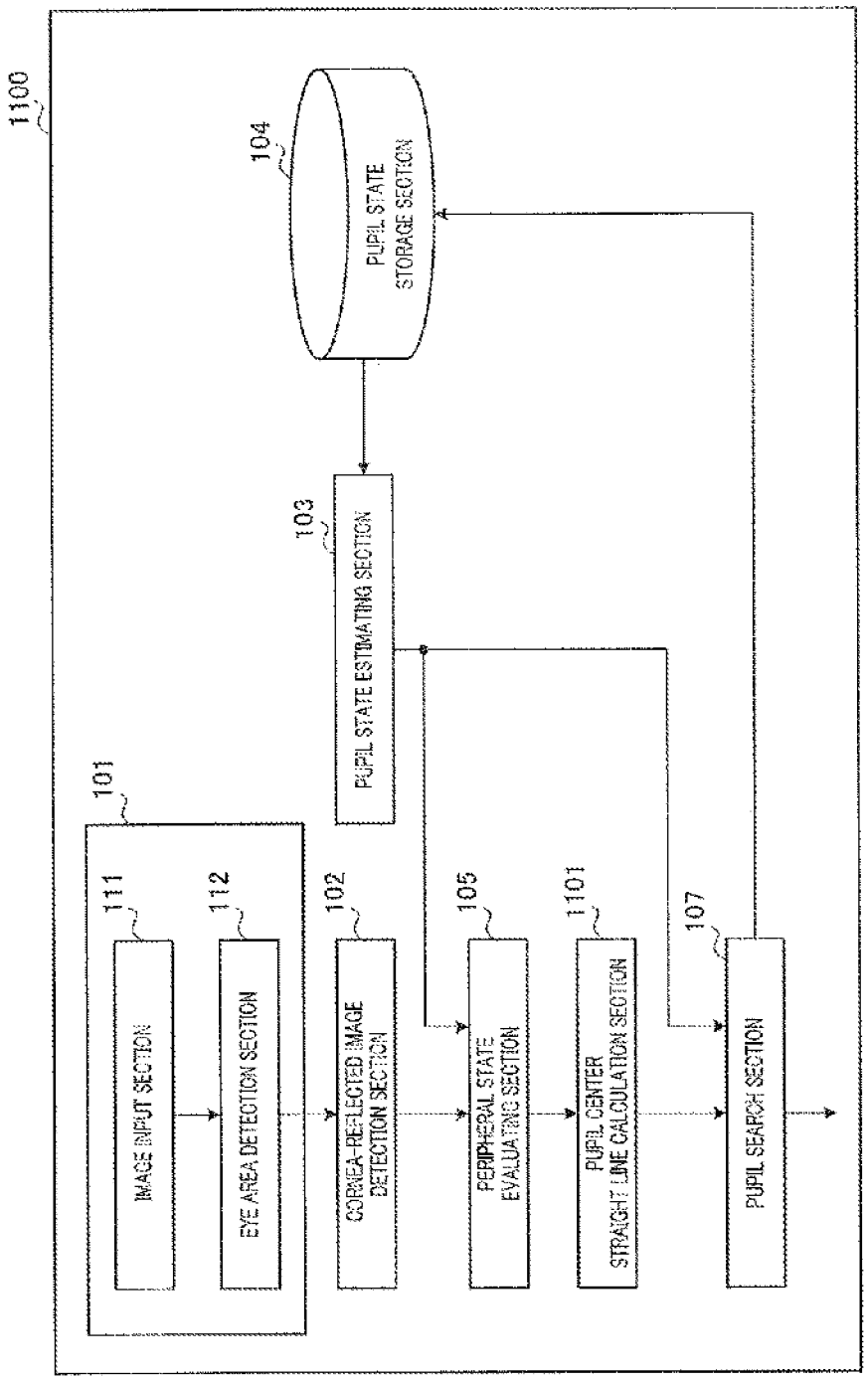
FIG. 14 is a block diagram illustrating a configuration of a pupil detection device according to Embodiment 5 of the present invention.

FIG. 14 is a block diagram illustrating a configuration of pupil detection device 1100 according to Embodiment 4 of the present invention. Referring to FIG. 14, pupil detection device 1100 includes pupil center straight line calculation section 1101.

Pupil center straight line calculation section 1101 specifies the pupil center straight line, based on the luminance evaluation value calculated by peripheral state evaluating section 105. Specifically, pupil center straight line calculation section 1101 specifies a line segment, which corresponds to a center angle of an angle range which is largest in the luminance evaluation value of the center among a plurality of angle ranges which have a predetermined angle width centering on any angle and in which luminance evaluation values are symmetric to each other based on the center in the correspondence relation, as the pupil center straight line. That is, pupil center straight line calculation section 1101 specifies a line segment corresponding to an angle having the highest luminance evaluation value, among a plurality of angles in which a distribution of luminance evaluation values is symmetric in the periphery.

In detail, pupil center straight line calculation section 1101 differentiates a curved line representing the correspondence relation by an angle and extracts an angle at which a differential value changes from positive to negative or vice versa. Then, pupil center straight line calculation section 1101 specifies a line segment corresponding to an angle having a highest luminance evaluation value within the extracted angle group, as the pupil center straight line.

Figure 15:
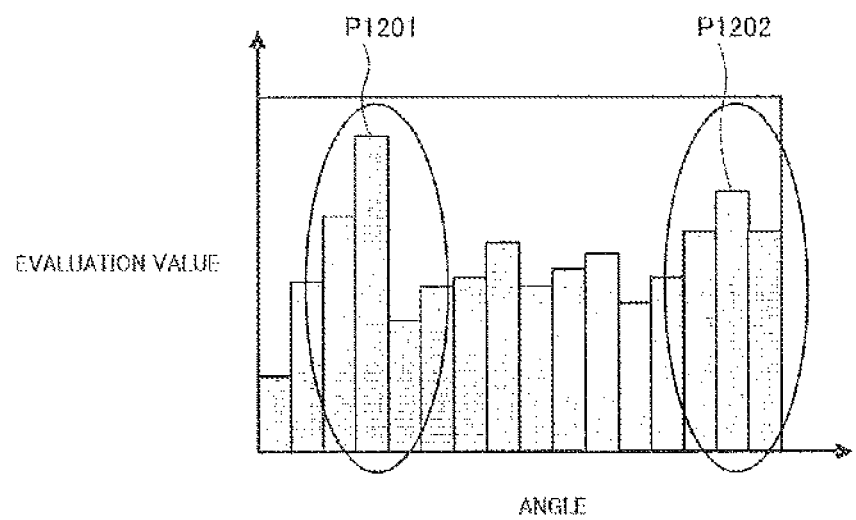
FIG. 15 is a diagram for describing an operation of a pupil center straight line calculation section.

According to this method of specifying the pupil center straight line, in FIG. 15, a peak P1201 is excluded, however, a peak P1202 is selected.

Here, the pupil has substantially a circular shape and thus has a shape which is line-symmetric to a straight line passing through the pupil center. For this reason, the luminance evaluation value also has a distribution symmetric centering on the pupil center straight line. As described above, by specifying the pupil center straight line using this characteristic, it is possible to reduce erroneous detection caused by that an angle other than an angle of a straight line passing through the pupil center has a highest luminance evaluation value, due to an erroneous detection factor such as noise of an image or eyelashes.

Embodiment 6

Embodiment 6 relates to a modification of the pupil search process.

Figure 16:
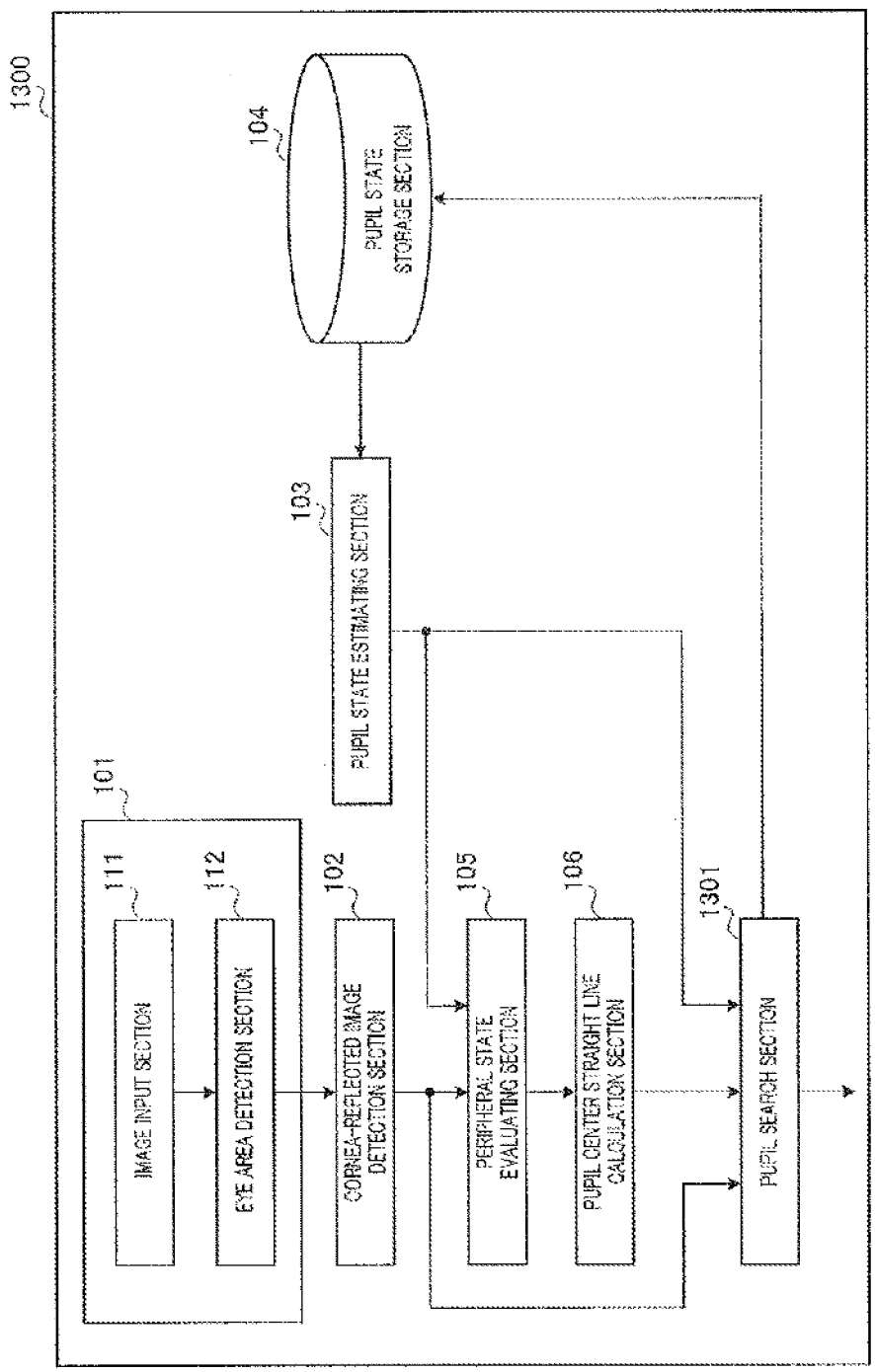
FIG. 16 is a block diagram illustrating a configuration of a pupil detection device according to Embodiment 6 of the present invention.

FIG. 16 is a block diagram illustrating a configuration of pupil detection device 1300 according to Embodiment 6 of the present invention. Referring to FIG. 16, pupil detection device 1300 includes pupil search section 1301.

Pupil search section 1301 searches for a pupil image based on the luminance state of the pupil center straight line. Specifically, pupil search section 1301 calculates a luminance gradient (a luminance gradient in a direction away from the center of the cornea-reflected image) in each point on the pupil center straight line from the luminance distribution of the image area created by cornea-reflected image detection section 102, and selects a point having a largest luminance gradient as a point on the contour of the pupil (that is, pupil contour point). Then, pupil search section 1301 detects a point which is distant by half of the estimated pupil diameter (that is, estimated pupil radius) from the pupil contour point toward the center of the cornea-reflected image on the pupil center straight line, as the pupil center.

Figure 17:
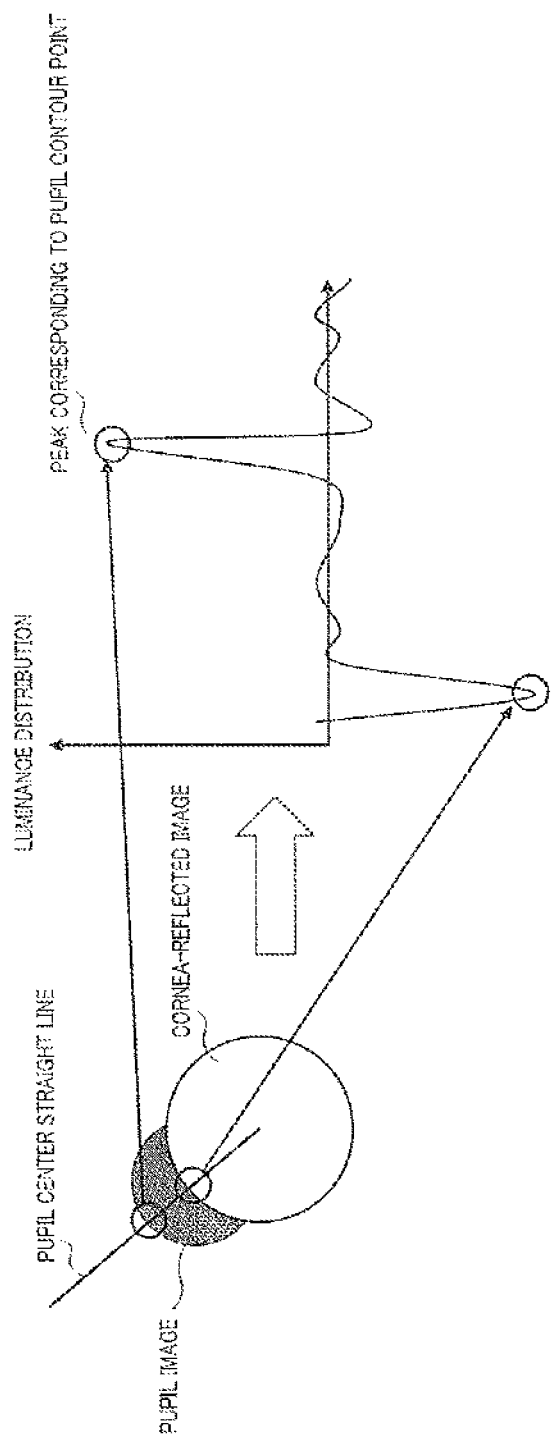
FIG. 17 is a diagram for describing an operation of a pupil search section.

That is, luminance becomes lower in order of the cornea-reflected image, the cornea image, and the pupil image. For this reason, when the luminance gradient in the direction that is distant from the center of the cornea-reflected image is calculated, the luminance gradient is reduced (that is, the luminance gradient becomes negative) in the boundary between the cornea-reflected image and the pupil image, and the luminance gradient is highest in the boundary between the pupil image and the cornea (excluding the cornea-reflected image portion) as illustrated in FIG. 17. Thus, as described above, the pupil contour point can be specified by selecting the point having the highest luminance gradient, and the pupil center can be specified from the pupil contour point.

Embodiment 7

Embodiment 7 relates to a modification of the pupil search process, similarly to Embodiment 6. In Embodiment 7, a separability filter is used for the pupil search process.

Figure 18:
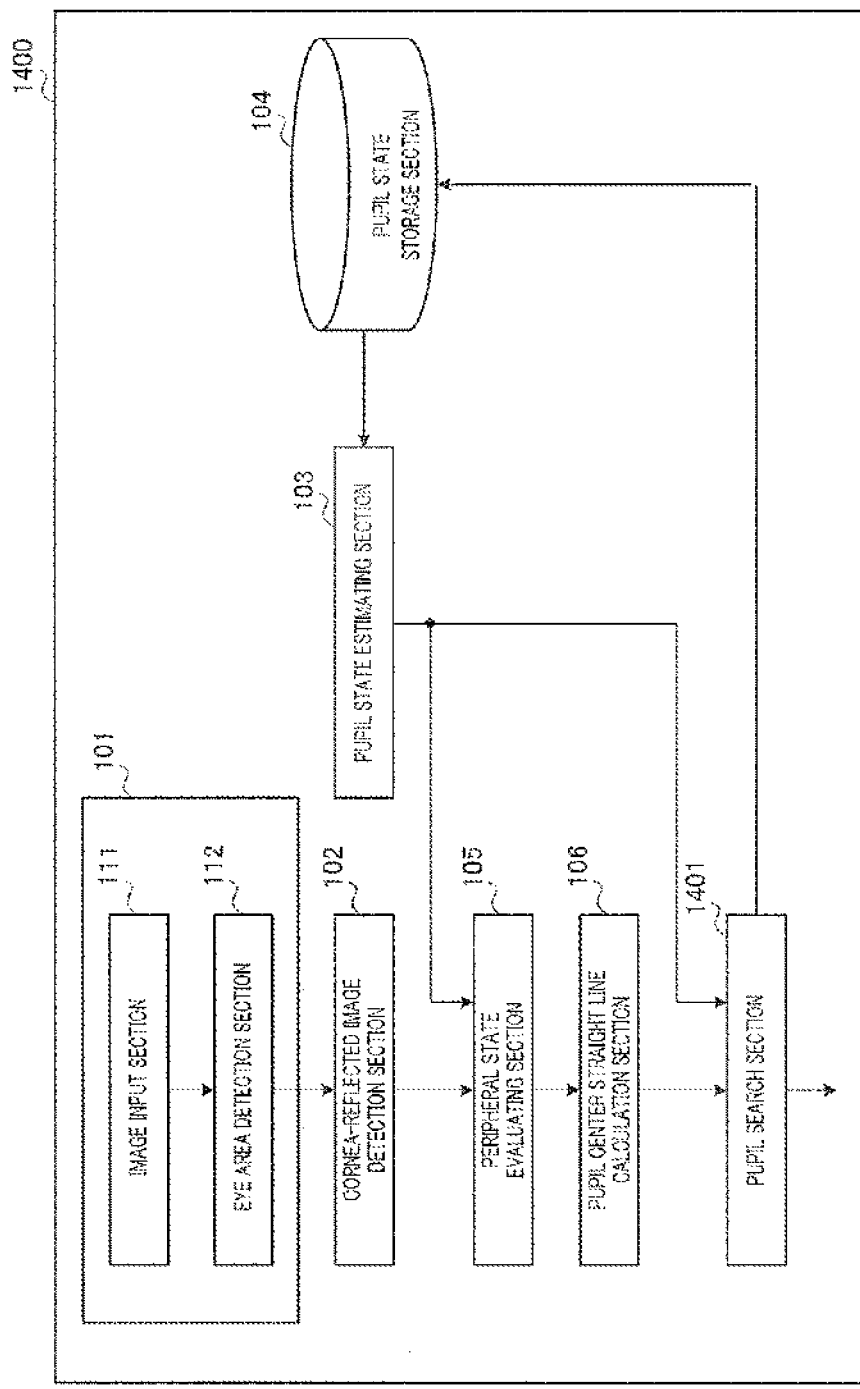
FIG. 18 is a block diagram illustrating a configuration of a pupil detection device according to Embodiment 7 of the present invention.

FIG. 18 is a block diagram illustrating a configuration of pupil detection device 1400 according to Embodiment 7 of the present invention. Referring to FIG. 18, pupil detection device 1400 includes pupil search section 1401.

Pupil search section 1401 searches for the pupil image based on the luminance state around the pupil center straight line. Specifically, pupil search section 1401 calculates separability η at each point where a reference point of a separability filter is positioned while sequentially moving the separability filter in a state in which the reference point is aligned on the pupil center straight line, and detects a point having the highest separability η as the pupil center.

Figure 19:
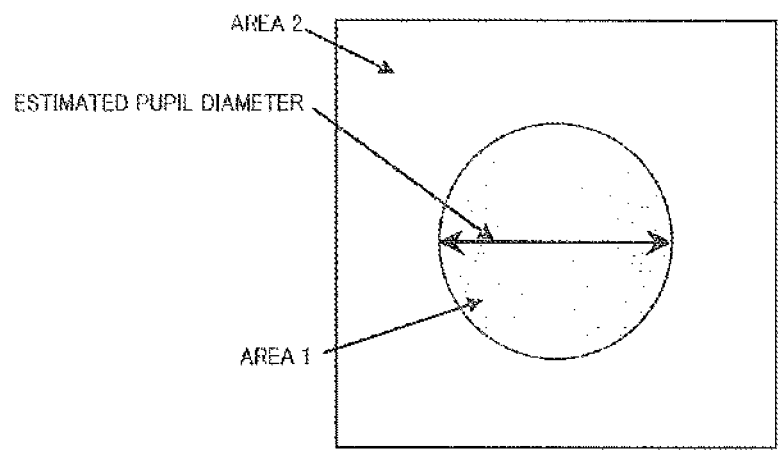
FIG. 19 is a diagram for describing an operation of a pupil search section.

Here, the separability filter is configured with a circular area 1 having the estimated pupil diameter as the diameter and an area 2 which is a peripheral area thereof as illustrated in FIG. 19. Further, the separability filter may be expressed by the following equation 3.

(Equation 3)

$$\eta = \frac{\sigma_b^2}{\sigma_T^2} \quad [3]$$

$$\sigma_b^2 = n_1(\overline{P_1} - \overline{P_m})^2 + n_2(\overline{P_2} - \overline{P_m})^2$$

$$\sigma_T^2 = \sum_{i=1}^{N}(\overline{P_i} - \overline{P_m})^2$$

In equation 3, $n_1$, $n_2$, and N represent the number of pixels of the area 1, the area 2, and the overall area (that is, the area 1+the area 2), respectively, $\sigma_T$ represents a total variance value of an overall area, and $\sigma_b$ represents a between-class variance value of the area 1 and the area 2. Further, $P_i$ represents a luminance value at a position i, and $P_1$, $P_2$, $P_m$ represent average luminance values of the area 1, the area 2, and the overall area, respectively. Here, when the cornea-reflected image is present in the area 1 or the area 2, the separability η is calculated by excluding the cornea-reflected image portion from the area 1 or the area 2.

That is, as the value of the separability η increases, luminance in each of the area 1 and the area 2 become more uniform, and a luminance difference between the area 1 and the area 2 tends to increase. Thus, when the area 1 matches with the pupil image and the area 2 matches with an iris image (an image area around the pupil image), the value of the separability η is highest. This is because luminance of the pupil image is low and luminance of the iris is high.

Thus, as described above, the pupil center can be specified by calculating the separability η at each point where the reference point of the separability filter is positioned while sequentially moving the separability filter in a state in which the reference point is aligned on the pupil center straight line, and specifying a point having the highest separability η as the pupil center.

The above embodiments have been described in connection with the example the present invention is implemented by hardware, however, the present invention may be implemented by software.

The functional blocks used for description of the above embodiments are typically implemented as large scale integration (LSI) which is an integrated circuit (IC). These may be individual chips or partially or totally contained on a single chip. "LSI" is adopted here but this may also be referred to as "IC," "system LSI," "super LSI," or "ultra LSI" depending on differing extents of integration.

Further, the method of circuit integration is not limited to LSI's, and implementation using dedicated circuitry or general purpose processors is also possible. After LSI manufacture, a field programmable gate array (FPGA) which is programmable or a reconfigurable processor where connections and settings of circuit cells within an LSI can be reconfigured may be used.

Further, if integrated circuit technology comes out to replace LSI's as a result of the advancement of semiconductor technology or a derivative other technology, it is naturally also possible to carry out function block integration using this technology. Application of biotechnology is also possible.

The pupil detection device described in the above embodiments is usefully applied to information terminals such as personal computers (PCs), office automation (OA) machines, and portable telephones or information provision devices mounted in transportation devices such as vehicles, airplanes, ships, and electric trains. Further, the pupil detection device can be applied to monitoring devices, alarming devices, robots, video/audio reproducing devices, and the like.

The disclosure of Japanese Patent. Application No. 2010-162964, filed on Jul. 20, 2010, including the specification, drawings and abstract, is incorporated herein by reference in its entirety.

INDUSTRIAL APPLICABILITY

The pupil detection device and the pupil detection method of the present invention can stably detect the pupil by actively using information of the cornea-reflected image even when most of the pupil is hidden by the cornea-reflected image.

| Reference Signs List | |
|---|---|
| 100, 600, 800, 1000, 1100, 1300, 1400 | Pupil detection device |
| 101 | Eye area image acquisition section |
| 102 | Cornea-reflected image detection section |
| 103 | Pupil state estimating section |
| 104 | Pupil state storage section |
| 105, 601 | Peripheral state evaluating section |
| 106, 1001, 1101 | Pupil center straight line calculation section |
| 107, 804, 1301, 1401 | Pupil search section |
| 111 | Image input section |
| 112 | Eye area detection section |
| 121 | Face detection section |
| 122 | Face part detection section |
| 123 | Eye area determination section |
| 602 | Sclera average luminance calculation section |
| 603 | Sclera average luminance storage section |
| 801 | Illuminance measuring section |
| 802 | Illumination state storage section |
| 803 | Illumination state estimating section |

The invention claimed is:

1. A pupil detection device that detects a pupil image in an eye area image, comprising:
   a first detection section that detects a cornea-reflected image that is a high luminance image area of the eye area image;
   an evaluation value calculation section that sets a plurality of line segments having a reference point of the cornea-reflected image as one end and having a predetermined length, and calculates a luminance evaluation value based on luminance of each pixel in each line segment and reference luminance;
   a specifying section that specifies a pupil center straight line passing through a center of the pupil image from among the plurality of line segments, based on the luminance evaluation value; and
   a second detection section that detects the pupil image based on a luminance state around the pupil center straight line or a luminance state of the pupil center straight line.

2. The pupil detection device according to claim 1, wherein the evaluation value calculation section compares luminance of each pixel with the reference luminance on each line segment, extracts a pixel having luminance lower than the reference luminance, and calculates a total sum of differences between luminance of all extracted pixels and the reference luminance, as the luminance evaluation value.

3. The pupil detection device according to claim 2, wherein the specifying section specifies a line segment having the largest luminance evaluation value, as the pupil center straight line.

4. The pupil detection device according to claim 1, wherein the second detection section sequentially sets pupil image area candidates whose centers are present on the pupil center straight line, and detects the pupil image based on an average luminance of a pixel group having luminance lower than the reference luminance among pixel groups of each of the set pupil image area candidate.

5. The pupil detection device according to claim 1, further comprising
   a sclera luminance calculation section that calculates luminance of a sclera present outside the pupil image based on a diameter of the pupil image detected by the second detection section,
   wherein the evaluation value calculation section sets the luminance of the sclera most recently calculated by the sclera luminance calculation section as the reference luminance.

6. The pupil detection device according to claim 4, wherein the second detection section adjust a diameter of the set pupil image area candidate according to illuminance.

7. The pupil detection device according to claim 2, wherein the specifying section sequentially shifts an average calculation range having a predetermined angle range, and specifies the pupil center straight line based on an average value of luminance evaluation values calculated by respective average calculation ranges.

8. The pupil detection device according to claim 2, wherein the specifying section specifies a line segment, which corresponds to an angle having the highest luminance evaluation value among a plurality of angles in which a distribution of a luminance evaluation value is symmetric in a periphery, as the pupil center straight line, in a correspondence relation between a luminance evaluation value calculated on each line segment and an angle between a reference direction and each line segment.

9. The pupil detection device according to claim 1, wherein the second detection section detects a contour point of the pupil image based on a luminance gradient on the pupil center straight line, and a point distant from the contour point by a pupil radius as a center of the pupil image.

10. The pupil detection device according to claim 1, wherein the second detection section sets a separability filter to a plurality of points on the pupil center straight line, and detects the pupil image based on separability calculated at each point.

11. A pupil detection method of detecting a pupil image in an eye area image, comprising:
    detecting a cornea-reflected image that is a high luminance image area of the eye area image;
    setting a plurality of line segments having a reference point of the cornea-reflected image as one end and having a predetermined length;
    calculating a luminance evaluation value based on luminance of each pixel in each line segment, and reference luminance;
    specifying a pupil center straight line passing through a center of the pupil image from among the plurality of line segments, based on the luminance evaluation value; and
    detecting the pupil image based on a luminance state around the pupil center straight line or a luminance state on the pupil center straight line.

* * * * *